US008232221B2

(12) United States Patent
Kuznicki

(10) Patent No.: US 8,232,221 B2
(45) Date of Patent: Jul. 31, 2012

(54) ZEOLITE SUPPORTED METALLIC NANODOTS

(75) Inventor: Steven M. Kuznicki, Edmonton (CA)

(73) Assignee: Governors of the University of Alberta, Edmonton, Alberta (CA)

( * ) Notice: Subject to any disclaimer, the term of this patent is extended or adjusted under 35 U.S.C. 154(b) by 871 days.

(21) Appl. No.: 11/777,804

(22) Filed: Jul. 13, 2007

(65) Prior Publication Data

US 2010/0021559 A1 Jan. 28, 2010

Related U.S. Application Data

(60) Provisional application No. 60/807,418, filed on Jul. 14, 2006.

(51) Int. Cl.
*B01J 29/06* (2006.01)
(52) U.S. Cl. .............. 502/60; 502/74; 502/75; 502/85; 502/214
(58) Field of Classification Search .............. 502/60, 502/74, 75, 85, 214
See application file for complete search history.

(56) References Cited

U.S. PATENT DOCUMENTS

| | | | | |
|---|---|---|---|---|
| 3,013,982 A | * | 12/1961 | Breck et al. | 252/181.6 |
| 3,013,985 A | * | 12/1961 | Breck et al. | 502/79 |
| 3,200,082 A | * | 8/1965 | Breck et al. | 502/74 |
| 3,248,170 A | * | 4/1966 | Kvetinskas | 423/718 |
| 4,673,559 A | * | 6/1987 | Derouane et al. | 423/701 |
| 4,744,805 A | | 5/1988 | Maroulis et al. | |
| 4,747,854 A | | 5/1988 | Maroulis et al. | |
| 4,874,525 A | | 10/1989 | Markovs | |
| 4,874,592 A | | 10/1989 | Shino et al. | |
| 5,069,698 A | | 12/1991 | Cheung et al. | |
| 5,071,804 A | | 12/1991 | Kuznicki et al. | |
| 5,122,173 A | | 6/1992 | Agrawal et al. | |
| 5,223,022 A | * | 6/1993 | Kuznicki et al. | 75/427 |
| 5,226,933 A | | 7/1993 | Knaebel et al. | |
| 5,470,378 A | | 11/1995 | Kandybin et al. | |
| 5,837,275 A | | 11/1998 | Burrell et al. | |
| 5,916,836 A | * | 6/1999 | Toufar et al. | 502/86 |
| 6,168,649 B1 | | 1/2001 | Jensvold et al. | |
| 6,432,170 B1 | | 8/2002 | Chiang et al. | |
| 6,544,318 B2 | | 4/2003 | Dee et al. | |
| 6,572,838 B1 | | 6/2003 | Sebastian et al. | |
| 6,953,494 B2 | | 10/2005 | Nelson, Jr. | |
| 2005/0203237 A1 | * | 9/2005 | Cornelius Maria Dekkers et al. | 524/450 |
| 2006/0008442 A1 | | 1/2006 | MacDonald et al. | |
| 2009/0202655 A1 | | 8/2009 | Kuznicki | |
| 2010/0021559 A1 | | 1/2010 | Kuznicki | |
| 2010/0050868 A1 | | 3/2010 | Kuznicki et al. | |

FOREIGN PATENT DOCUMENTS

| | | |
|---|---|---|
| CA | 2563727 | 9/2005 |
| EP | 1604953 | 12/2005 |
| WO | 9104096 | 4/1991 |
| WO | 9621745 | 7/1996 |
| WO | 2005087855 | 9/2005 |
| WO | 2008070988 | 6/2008 |

OTHER PUBLICATIONS

Durham, M.D. et al.; Field Test Program to Develop Comprehensive Design, Operating and Cost Data for Mercury Control Systems on Non-Scrubbed Coal-Fired Boilers; Air & Waste Management Association 84th Annual Meeting and Exhibition; 2001; Orlando, Florida, USA.
Erickson, B.E.; Regnerating Mercury-Loaded Sorbents; Environmental Science & Technology; 2002; pp. 408A-409A; American Chemical Society.
Granite, E.J. et al.; Novel Sorbents for Mercury Removal from Flue Gas; Ind. Chem. Res.; 2000; vol. 39; pp. 1020-1029; American Chemical Society.
Hall, B. et al.; Chemical Reactions of Mercury in Combustion Flue Gases; Water, Air and Soil Pollution; 1991; vol. 56; pp. 3-14; Kluwer Academic Publishers.
Hayhurst, D.T.; The Potential of Use of Natural Zeolites for Ammonia Removal During Coal-Gasification; Natural Zeolites: Occurrence; 1978; pp. 503-507; Use Permagon Press.
Holmes, M. et al.; Mercury Information Clearinghouse: Quarterly 1—Sorbent Injection Technologies for Mercury Control; U.S.D.O. E.#DE-FC26-98FT40321; 21 pages; http://www.ceamercuryprogram.ca.
Lewis, L.N.; Chemical Catalysis by Colloids and Clusters; Chemical Review; 1993; vol. 93; pp. 2693-2730; America Chemical Society.
Massalski, T.B.; Binary Alloy Phase Diagrams; ASM International, Materials Park; 1990; vol. 1; pp. 43-45; Ohio.
Miller, S.J. et al.; Flue Gas Effects on a Carbon-Based Mercury Sorbent; Fuel Processing Technology; 2000; vol. 65-66; pp. 343-363; Elsevier Science.
Miller, B.G.; Pollutants with Pending Compliance Regulation; Coal Energy Systems; 2005; pp. 369-373; Elsevier.
Mondale, K.D. et al.; The Comparative Ion Exchange Capacities of Natural Sedimentary and Synthetic Zeolites; Minerals Engineering; 1995; vol. 8, No. 4/5; pp. 535-548; Elsevier Science Ltd.
Morris, T. et al.; The Effects of Mercury Adsorption on the Optical Response of Size-Selected Gold and Silver Nanoparticles; Langmuir; 2002; vol. 18; pp. 7261-7264; American Chemical Society.
Mottet,C. et al.; Single Impurity Effect on the Melting of Nanoclusters; Physical Review Letters; 2005; vol. 95; pp. 035501-1-035501-4; The American Physical Society.
Nelson, S. Jr. et al.; Accumulated Power-Plant Mercury-Removal Experience with Brominated PAC Injection; Combined Power Plant Air Pollutant Control Mega Symposium; 2004; Washington, DC, USA.
Pavlish, J.H. et al.; Technical Review of Mercury Technology Options for Canadian Utilities—A Report to the Canadian Council of Ministers of the Environment; Final Report for the Canadian Council of Ministers of the Environment; 2005; 22 pages; Winnipeg, Manitoba, Canada.
Seidel, A. et al.; Copper Nanoparticles in Zeolite Y; Journal of Materials Chemistry; 1999; vol. 9; pp. 2495-2498; J. Mater. Chem.

(Continued)

*Primary Examiner* — Elizabeth Wood
(74) *Attorney, Agent, or Firm* — Bennett Jones LLP

(57) ABSTRACT

A metal nanodot material is formed by ion-exchange with chabazite or a chabazite-like structure, followed by activation to form metallic nanodots. The nanodot may be formed from silver, nickel, copper, gold or a platinum group metal.

9 Claims, 6 Drawing Sheets

OTHER PUBLICATIONS

Senior, C.L.; Impact of Carbon-in-Ash on Mercury Removal Across Particulate Control Devices in Coal-Fired Power Plants; Energy & Fuels; 2005; vol. 19; pp. 859-863; American Chemical Society.

Shvartsburg, A.A. et al.; Solid Clusters Above the Bulk Melting Point; Physical Review Letters; 2000; vol. 85, No. 12; pp. 2530-2532; The American Physical Society.

Sobral, L.G.S. et al.; Electrolytic Treatment of Mercury-Loaded Activated carbon From a Gas Cleaning System; The Science of the Total Environment; 2000; vol. 261; pp. 195-201; Elsevier Science B.V.

Vidic, R.D. et al.; Vapor-Phase Elemental Mercury Adsorption by Activated Carbon Impregnated with Chloride and Chelating Agents; Carbon; 2001; vol. 39; pp. 3-14; Elsevier Science Ltd.

GSA Resources, Inc.; www.gsaresources.com.

Baerlocher, Ch. et al.; Altas of Zeolite Framework Types; 2001; 5th rev. ed.; Amsterdam; Elsevier.

Hall, Bjorn et al.; Mercury Chemistry in Simulated Flue Gases Related to Waste Incineration Conditions; Environ. Sci. Technol.; 1990; vol. 24, No. 1; pp. 108-111; American Chemical Society.

Thrush, Kathleen A. et al.; Characterization of Chabazite and Chabazite-like Zeolites of Unusual Composition; J. Chem Soc.; 1991; vol. 87(7); pp. 1031-1035; Royal Society of Chemistry.

Breck, D.W.; Zeolite Molecular Sieves; 1974; pp. 31-32; John Wiley; New York.

Barrer, R.M. et al.; Mercury Uptake in Cationic Forms of Several Zeolites; Journal of The Chemical Society; 1967; pp. 19-25; Section A, Inorganic, Physical, and Theoretical Chemistry, Part 1; London: The Chemical Society.

Jin, R. et al.; Controlling Anisotropic Nanoparticle Growth Through Plasmon Excitation; Nature; 2003; vol. 425; pp. 487-490; Nature Publishing Group.

Jin, R. et al.; Photoinduced Conversion of Siver Nanospheres to Nanoprisms; Science; 2001; vol. 294; pp. 1901-1903.

Callegari, A. et al.; Photochemically Grown Silver Nanoparticles with Wavelength-Controlled Size and Shape; Nano Letters; 2003; vol. 3, No. 11; pp. 1565-1568; American Chemical Society.

Sun, Y et al.; Transformation of Siver Nanosperes into Nanobelts and Triangular Nanoplates Through a Thermal Process; Nano Letters; 2003; vol. 3, No. 5; pp. 675-679; American Chemical Society.

Xia, Y. et al.; One-Dimensional Nanostructures: Synthesis, Characterization, and Applications; Advanced Materials; 2003; vol. 15, No. 5; pp. 353-389; Wiley-Vch Verlag GmbH & Co.

Chen, S. et al.; Synthesis and Charcterization of Truncated Triangular Silver Nanoplates; Nano Letters; 2002; vol. 2, No. 9; pp. 1003-1007; American Chemical Society.

Zhou, Y. et al.; A Novel Ultraviolet Irradiation Technique for Shape-Controlled Synthesis of Gold Nanoparticles at Room Temperature; Chemical Materials; 1999; vol. 11; pp. 2310-2312; American Chemical Society.

Edmondson, M.J. et al.; Electron-Beam Induced Growth of Bare Silver Nanowires from Zeolite Crystallites; Advanced Materials; 2001; vol. 13, No. 21; pp. 1608-1611; Wiley-Vch Verlag GmbH & Co.

Li, C. et al.; In Situ Observation of Bamboo-Shoot-Like One-Dimensional Growth of SiOx-AgyO Nanowires Induced by Electron Beam Irradiation; Materials Letters; 2004; vol. 58; pp. 3573-3577; Science Direct.

Worboys, L.M. et al.; Silver Nanowires: Inclusion in and Extrusion from Mesoporous Supports; Studies in Surface Science and Catalysis; 2004; vol. 154; pp. 931-938; Elsevier B.V.

Tsapatsis, M.; Molecular Sieves in the Nanotechnology Era; Perspective; 2002; vol. 48, No. 4; pp. 654-660; American Institute of Chemical Engineers.

Strohal, R. et al.; Nanocrystalline Silver Dressings as an Efficient Anti-MRSA Barrier: A New Solution to an Increasing Problem; Science Direct; Journal of Hospital Infection; 2005; vol. 60; pp. 226-230; Elsevier Ltd.

Metraux, G.S. et al.; Rapid Thermal Synthesis of Silver Nanoprisms with Chemically Tailorable Thickness; Advanced Materials; 2005; vol. 17, No. 4; pp. 412-415; Wiley-Vch Verlag GmbH & Co.

Gellens, L.R. et al.; Oxidation and Reduction of Silver in Zeolite Y: A Structural Study; Zeolites; 1981; vol. 1; pp. 85-90; IPC Business Press.

Gurin, V.S. et al.; Metal Clusters and Nanoparticles Assembled in Zeolites: An Example of Stable Materials with Controllable Particle Size; Materials Science & Engineering; 2002; vol. 19; pp. 327-331; Elsevier Science B.V.

Gurin, V.S. et al.; Silver and Copper Nanostructures Within the Erionite Regular Lattice: Interplay Between Intra- and Extra-Crystalline Location; Materials & Science Engineering; 2003; vol. C23; pp. 81-85; Elsevier Science B.V.

Gurin, V.S. et al.; Silver and Copper Clusters and Small Particles Stabilized Within Nanoporous Silicate-Based Materials; Materials Science & Engineering; 2005; vol. A 391; pp. 71-76; Elsevier B.V.

Bagnasco, G. et al.; Oxidation of Ethylene on Silver-Loaded Natural Zeolites; 1982; pp. 275-283; Elsevier.

Cho, S.J. et al.; Effect of Multivalent Cations on Agglomeration of Ru Clusters Supported on Y Zeolite; Catalysis; 2000; vol. 71, No. 3-4; Plenum Publishing Corporation.

Alt, V. et al.; An In Vitro Assessment of the Antibacterial Properties and Cytotoxicity of Nanoparticulate Silver Bone Cement; Biomaterials; 2005; vol. 25; pp. 4383-4391; Elsevier Ltd.

Anderson, M.W. et al.; Structure of the Microporous Titanosilicate ETS-10; Letters to Nature; 1994; vol. 367, No. 27; pp. 347-351; Nature Publishing Group.

Anderson, M.W. et al.; Microporous Titansilicate ETS-10: A Structural Survey; Philosophical Magazine B; 1995; vol. 71, No. 5; pp. 813-841; Taylor & Francis Ltd.

Sankar, G. et al.; Determination of the Structure of Distorted TIO6 Units in the Titanoisilicate ETS-10 by a Combination of X-ray Absorption Spectroscopy and Computer Modeling; J. Phys. Chem.; 1996; vol. 100; pp. 449-452; American Chemical Society.

Sun, T. et al.; Silver Clusters and Chemistry in Zeolites; Chemical Reviews; 1994; vol. 94, No. 4; pp. 857-870; American Chemical Society.

Hutson N.D. et al.; Silver Ion-Exchanged Zeolites Y, X, and Low-Silica X: Observations of Thermally Induced Cation/Cluster Migration and the Resulting Effects on the Equilibrium Absorption of Nitrogen; Chemical Matters; 2000; vol. 12, No. 10; pp. 3020-3031; American Chemical Society.

Sebastian, J. et al.; Sorption of Nitrogen, Oxygen, and Argon in Silver-Exchanged Zeolites; Ind. Eng. Chem. Res.; 2005; vol. 44, No. 21; pp. 8014-8024; American Chemical Society.

Grosse, R. et al.; 129Xe NMR of Silver-Exchanged X- and Y-Type Zeolites; J. Phys. Chem.; 1991; vol. 95, No. 6; pp. 2443-2447; American Chemical Society.

Grosse, R. et al.; Absorption and 129 Xe n.m.r. of Xenon in Silver-Exchanged Y Zeolites: Application to the Location of Silver Cations; Zeolites; 1992; vol. 12; pp. 909-915; Butterworth-Heinemann.

Watermann, J. et al.; Isoteric Heats of Adsorption of Xenon in Silver-Exchanged Y Zeolites; Zeolites; 1993; vol. 13; pp. 427-429; Butterworth-Heinemann.

Munakata, K. et al.; Absorption of Noble Gases on Silver-Mordenite; Journal of Nuclear Science and Technology; vol. 40, No. 9; pp. 695-697.

Lynch, C. et al.; Xenon Anesthesia; Clinical Concepts and Commentary; 2000; vol. 92, No. 3; Anesthesiology.

Hammarlund, N.; The Krypton and Xenon Markets Up to the Year 2000; Nuclear Instruments & Methods in Physics Research; 1992; vol. A316; pp. 83-87; Elsevier Science Publishers B.V.

Lard, E.W. et al.; Separation and Determination of Argon, Oxygen, and Nitrogen by Gas Chromatography; Analytical Chemistry; 1960; vol. 32, No. 7; pp. 878-879.

Jones, K. et al.; Separation and Determination of Argon and Oxygen in High-Purity Nitrogen Streams by Gas Chromatography; Nature; 1964; vol. 202, No. 4936; pp. 1003-1004; Nature Publishing Group.

Walker, J.A.J. et al.; Chromatographic Separation of Argon and Oxygen Using Molecular Sieve; 1966; No. 5019; pp. 197; Nature Publishing Group.

Pollock, G.E. et al.; Gas Chromatographic Separation of Nitrogen, Oxygen, Argon, and Carbon Monoxide Using Custom-Made Porous Polymers from High Purity Divinylbenzene; Journal of Chromatographic Science; 1984; vol. 22; pp. 343-347.

Pollock, G.E.; Synthesis of a Further Improved Porous Polymer for the Separation of Nitrogen, Oxygen, Argon, and Carbon Monoxide by Gas Chromatography; Technical Note; 1986; vol. 24; pp. 173-174; Journal of Chromatographic Science.

Maroulis, P.J. et al.; Calcium Chabazite Adsorbent for the Gas Chromatographic Separation of Trace Argon-Oxygen Mixtures; Anal. Chem.; 1989; vol. 61; pp. 1112-1117; American Chemical Society.

Rege, S.U. et al.; Kinetic Separation of Oxygen and Argon Using Molecular Sieve Carbon; Adsorption; vol. 6; pp. 15-22; Kluwer Academic Publishers.

Jin, X. et al.; Production of Argon from an Oxygen-Argon Mixture by Pressure Swing Adsorption; Ind. Eng. Chem. Res.; 2006; vol. 45, No. 16; pp. 5775-5787; American Chemical Society.

Sebastian, J. et al.; Anomalous Adsorption of Nitrogen and Argon in Silver Exchanged Zeolite A; ChemComm; 2003; pp. 268-269; The Royal Society of Chemistry.

Yang, R.T. et al.; Zeolites Containing Mixed Cations for Air Separation by Weak Chemisorption-Assisted Adsorption; Ind. Eng. Chem. Res.; 1996; vol. 35, No. 9; pp. 3093-3099; American Chemical Society.

Dewar, M.J.S.; A Review of the Complex Theory; Colloque International de Montpellier; 1951; vol. C71.

Hutson, N.D. et al.; Mixed Cation Zeolites: Lix Agy-X as a Superior Adsorbent for Air Separation; Separations; 1999; vol. 45, No. 4; pp. 724-734; American Institute of Chemical Engineers.

Salla, I. et al.; Study of the Influence of Several Mordenite Modifications on Its N2 and O2 Adsorption Properties; J. Phys. Chem.; 2004; vol. 108; pp. 5359-5364; American Chemical Society.

Diaz, E. et al.; Evaluation of Adsorption Properties of Zeolites Using Inverse Gas Chromatography: Comparison With Immersion Calorimetry; Thermochimica Acta; 2005; vol. 434; pp. 9-14; Elsevier B.V.

Zangwill, A.; Thermodynamics; Physics at Surfaces; 1988; pp. 192-194; Cambridge University Press.

Huheey, J.E.; Bond Energies and Bond Lengths; Inorganic Chemistry, 3rd Ed.; 1983; Appendix E; pp. A-28-A-44; Harper & Row.

Kuznicki, S.M. et al.; Metal Nanodots Formed and Supported on Chabazite and Chbazite-Like Surfaces; Microporous and Mesoporous Materials; 2007; vol. 103; pp. 309-315; Elsevier Inc.

* cited by examiner

ZEOLITE SUPPORTED METALLIC NANODOTS

CROSS REFERENCE TO RELATED APPLICATIONS

This application claims the priority benefit of U.S. Provisional Patent Application No. 60/807,418 filed on Jul. 14, 2006 entitled "Zeolite Supported Metallic Nanoclusters and Uses Thereof", the contents of which are incorporated herein by reference.

FIELD OF THE INVENTION

The present invention relates to metal nanodots formed on chabazite and chabazite analogs.

BACKGROUND

Metal nanoparticles and nanowires are the subject of current research efforts motivated by their high potential utility derived from nanoscale induced optical, electrical and chemical properties.

A wide range of techniques has been reported to synthesize metal nanoparticles including numerous high vacuum approaches as well as a range of photochemical [1-3] and thermal methods [4-7]. A technique that is just beginning to gain attention is the potential use of zeolite surfaces to induce the growth of metal nanostructures [8-10]. With many of their properties manifested on a nano and subnano dimensional scale, molecular sieves would appear to be excellent candidates to be in the vanguard of such nanofabrication efforts [11].

Unfortunately, current techniques for nanosilver generation are expensive and cumbersome [14]. Subnanometer silver ensembles can be induced to form within zeolite cavities under certain conditions [15-18], and much larger configurations often form on zeolite surfaces under reductive atmospheres. While metals readily congregate on zeolite surfaces, achieving stable, zeolite supported metal nanoscale structures has proved difficult because of the high metal mobility generally seen on zeolite surfaces. Typically, upon reduction, metals ion-exchanged into zeolite crystals diffuse to the crystal surface and rapidly coalesce into micron-scale agglomerates [19, 20]. Because of the low surface to volume ratio of these agglomerates (compared to nanometal ensembles), they generally behave like bulk metals, not displaying the novel properties anticipated for nanoparticulates.

Nanoparticulate silver has many potential uses. Many useful properties might be expected if inexpensive nanostructured silver materials were readily available. Silver is a well-known antimicrobial agent and nanoscale silver is finding increasing usage in bandages and related medical applications [12, 13]. Nano-silver particulates are on the forefront of infection control in medical devices and bandages [13]. Current methods to generate nanosilver center on complex techniques such as surface sputtering. Research level work in biomedical engineering implants is showing promise in nanosilver bone cements where nanoparticle size control ranges from 5 nm to 50 nm [24]. Powerful surface plasmon absorption of nanoparticulate silver makes them particularly useful in applications such as biosensors, for example. Silver nanodots may be photo-fluorescence markers, which make them useful for a number of medical and similar applications. They are environmentally and biologically benign. Other exemplary silver nanodot applications include smart windows, rewritable electronic paper, electronic panel displays, memory components, and others.

A wide range of techniques has been reported to synthesize metal nanodots. Silver nanodots and their formation have recently been discussed by Metraux and Mirkin, 2005 [14]. Traditional methods for the production of silver nanodots require use of potentially harmful chemicals such as hydrazine, sodium borohydride and dimethyl formamide ("DMF"). These chemicals pose handling, storage, and transportation risks that add substantial cost and difficulty to the production of silver nanodots. A highly trained production workforce is required, along with costly production facilities outfitted for use with these potentially harmful chemicals.

Another disadvantage of known methods for producing silver nanodots relates to the time and heat required for their production. Known methods of production utilize generally slow kinetics, with the result that reactions take a long period of time. The length of time required may be shortened by some amount by applying heat, but this adds energy costs, equipment needs, and otherwise complicates the process. Known methods generally require reaction for 20 or more hours at elevated temperatures of 60° to 80° C., for example. The relatively slow kinetics of known reactions also results in an undesirably large particle size distribution and relatively low conversion. The multiple stages of production, long reaction times at elevated temperatures, relatively low conversion, and high particle size distribution of known methods make them costly and cumbersome, particularly when practiced on a commercial scale.

While silver ensembles are well known to form within zeolite cavities under certain conditions, and much larger configurations often form freely on zeolite surfaces, nanodots have not been known to form on zeolite surfaces.

These and other problems with presently known methods for making silver nanodots are exacerbated by the relatively unstable nature of the nanodots. Using presently known methods, silver nanodots produced have only a short shelf life since they tend to quickly agglomerate.

Therefore, there is a need in the art for a convenient and inexpensive method of forming metal nanodots, such as silver nanodots, which mitigates the difficulties of the prior art.

SUMMARY OF THE INVENTION

In one aspect, the invention comprises a method of forming metal nanodots on a zeolite surface. Metal ion-exchange with the zeolite is followed by activating at moderate temperatures. In one embodiment, the zeolite comprises a chabazite or a chabazite analogue. In another aspect, the invention comprises a chabazite supported plurality of metal nanodots, formed by ion-exchange and subsequent activation. In one embodiment, the metal may comprise a transition or noble metal, for example, copper, nickel, palladium or silver.

In one embodiment, silver is a preferred metal. In one embodiment, silver nanodots may form having diameters less than about 100 nm, for example, less than about 50 nm, 30 nm, 20 nm, or 10 nm. In one embodiment, the nanodots are in the order of about 1 to about 5 nm, with a mean of about 3 nm, forming under a wide range of conditions on chabazite surfaces. In our testing, these nanodots are stable to at least 500° C. on the chabazite surfaces and remain as uniform nanodots under prolonged heating at elevated temperatures. Twenty (20%) percent by weight, or more, of a zeolite metal nanodot composite material may be composed of these silver particles.

Thus, in one preferred embodiment, an approach based on zeolite templated surface growth provides the capability to transfer such synthesis routes from tightly-controlled laboratory environments to large scale industrial chemical processes, where zeolites are already commonly used.

The present invention is distinctly different from the well established science of growing metal nanodots or nanowires within a zeolite cage framework, thus producing nanostructures inside the material. In the present invention, unlike in the prior art, the metallic nanodots are surface-accessible on the zeolite support.

Nanostructured silver materials produced in accordance with the present invention may have many useful properties. In one aspect, the invention may comprise the use of nanodots of silver to reversibly adsorb mercury at high temperatures. In another aspect, the invention may comprise the use of nanodots of silver as an antibacterial and/or antifungal agent.

Therefore, in one aspect, the invention may comprise a method of forming a metal nanoparticulate material, comprising the steps of:
(a) performing ion-exchange with a solution of the metal ions and a chabazite material; and
(b) activating the ion-exchanged chabazite material.

In another aspect, the invention may comprise a chabazite supported metal nanoparticulate material, comprising surface-accessible particles of metal, having a substantially uniform particle size less than about 100 nm, for example, less than about 50 nm, 30 nm, 20 nm, or 10 nm. In one embodiment, the material may comprise metal nanodots having a diameter less than about 5 nm.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

Figure 1A:
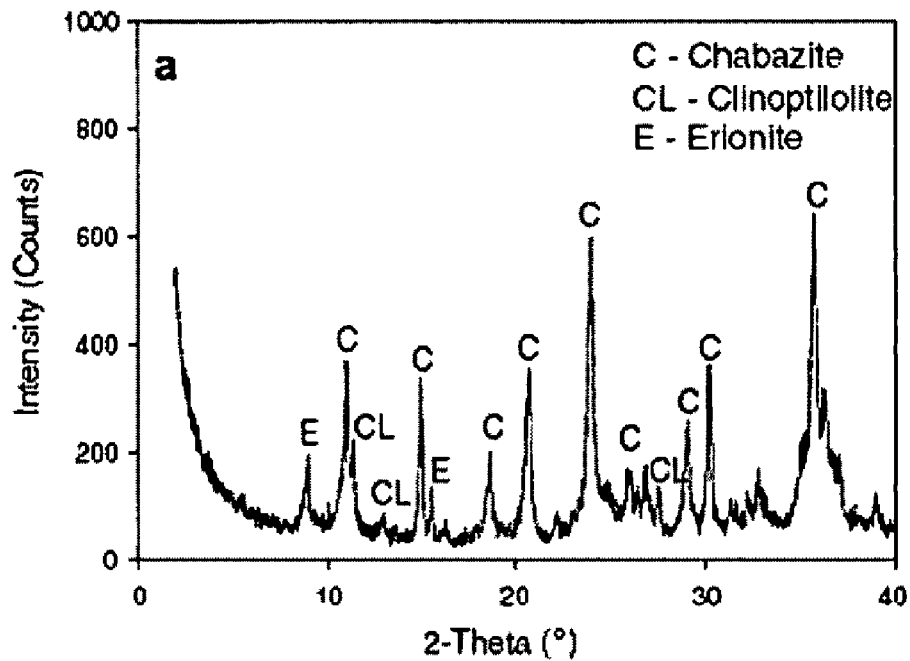
FIGS. 1A and 1B show powder X-ray diffraction spectra for raw chabazite and for upgraded semi-synthetic chabazite.

The present invention relates to metallic nanodots formed on chabazite or a chabazite-like material. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Although consistent terminology has yet to emerge, those skilled in the art generally consider "nanoclusters" to refer to smaller aggregations of less than about 20 atoms. "Nanodots" generally refer to aggregations having a size of about 10 nm or less. "Nanoparticles" are generally considered larger than nanodots, up to about 200 nm in size. In this specification, the term "nanodots" shall be used but is not intended to be a size-limiting nomenclature, and thus may be inclusive of nanoclusters and nanoparticles.

The term "about" shall indicate a range of values +/−10%, or preferably +/−5%, or it may indicate the variances inherent in the methods or devices used to measure the value.

As used herein, "chabazite" includes mineral chabazite, synthetic chabazite analogs such as zeolite D, R, G and ZK-14, and any other material with a structure similar or related to mineral chabazite. Chabazite and chabazite-like structures comprise a family of tectosilicate zeolitic materials [25] ranging from relatively high silica to stoichiometric 1/1 silica/aluminum materials. Synthetic analogs may be derived from any aluminosilicate source, such as kaolin clay. Thus, chabazite may include high-aluminum analogs such as those described in U.S. Pat. No. 6,413,492, the contents of which are incorporated herein by reference. Mineral chabazite may be upgraded such as by the methods described in Kuznicki et al "Chemical Upgrading of Sedimentary Na-Chabazite from Bowie, Ariz.", Clays and Clay Min. June 2007, 55:3, 235-238. One example of chabazite is exemplified by the formula: $(Ca,Na_2,K_2,Mg)Al_2Si_4O_{12}.6H_2O$. Recognized varieties include, but may not be limited to, Chabazite-Ca, Chabazite-K, Chabazite-Na, and Chabazite-Sr depending on the prominence of the indicated cation. Chabazite crystallizes in the trigonal crystal system with typically rhombohedral shaped crystals that are pseudo-cubic. The crystals are typically but not necessarily twinned, and both contact twinning and penetration twinning may be observed. They may be colorless, white, orange, brown, pink, green, or yellow. Chabazite is known to have more highly polarized surfaces than other natural and synthetic zeolites.

In general terms, in one embodiment, metal nanodots may be formed on a chabazite surface by ion-exchange of the metal cation into the chabazite, followed by an activating step, resulting in the formation of metal nanodots. In one embodiment, the metal is one of silver, copper, nickel, gold or a member of the platinum group. As used herein, a "platinum group" metal is ruthenium, rhodium, palladium, osmium, iridium or platinum. Generally, silver, gold and the platinum group are self-reducing. The use of salts of these metals will generally result in the formation of metal nanodots without the imposition of reducing conditions. However, the use of reducing conditions for such metals is preferable, if only to minimize oxidation of the metal. Generally, copper and nickel are reducible and their metal salts will generally result in the formation of metal nanodots upon reduction in a reducing atmosphere.

In a preferred embodiment, the metal comprises silver or nickel.

In one embodiment, silver chabazite may be prepared by ion-exchange of chabazite samples. For example, the chabazite as a fine powder (200 mesh) may be exposed to an excess of aqueous silver nitrate. In one embodiment, ion-exchange takes place at room temperature with stirring for 1 hour. The material may then be washed and dried. The silver ions in the zeolite may then be converted to metallic silver nanodots, supported on the chabazite, by an activation step. In one embodiment, the activation step may simply comprise the step of drying the material at room temperature. In a preferred embodiment, the activation step may comprise annealing the material at an elevated temperature, such as from 100° C. to 500° C. or higher, and preferably between about 100° to about 400° C. The activation step may take from 1 to 4 hours, or longer. In one embodiment, the activating step is performed in a reducing environment.

In one embodiment, the nanodots have a size less than about 100 nm, for example less than about 50 nm, less than about 30 nm or less than about 20 nm. In one embodiment, a substantial majority of the metal nanodots formed has a particle size of less than about 10 nm. In one preferred embodiment, a substantial majority is seen to be less than about 5 nm. In a preferred embodiment, the particles have a size distribution similar to that shown in FIG. 3, with a mean particle size about 3 nm.

In general, the size of the nanodots appears to be influenced by reducing or oxidizing conditions of the activating step. In one embodiment, the use of reducing conditions results in generally larger nanodot sizes. Conversely, the use of mild oxidizing conditions, such as air, results in generally smaller nanodot sizes.

Without being restricted to a theory, it is believed that the activating process causes the silver ions to migrate to the surface of the chabazite, where they reside as nanodots rather than as large particles or sheets. The silver ions reduce to their metallic state, before or after nanodot formation. Although the exact mechanism of the nanodot formation is not known, their scale and uniform distribution are likely due to the unusually highly polarized chabazite surface relative to other natural and synthetic zeolites [30-32]. As a result, the chabazite surface may have a significant electronic interaction with the clusters. This may stabilize particles containing a specific number of atoms (electronic charge consideration) or that are located at specific regions of the substrate, such as at steps or at kinks. Another rate limiting step may actually be the surface diffusion of the silver atoms, which is also affected by the charge. It may be that once the silver has migrated from the chabazite interior onto the surface, it becomes essentially "locked-in", able to neither diffuse back into the bulk nor migrate over the surface to join the larger clusters. An additional factor that will promote nanodot stability is the narrowness of the observed size distribution, which will reduce the driving force for Ostwald ripening.

In a preferred embodiment, chemically upgraded chabazite may induce the formation of more uniform metallic nanodots at higher concentrations. While samples of large crystals of essentially pure chabazite are well known (for example from Wasson Bluff, Nova Scotia, Canada), large, commercially exploitable deposits, like those found at Bowie, Ariz., invariably have the chabazite co-formed with significant amounts of other natural zeolites such as clinoptilolite and erionite.

It is known that raw sodium Bowie chabazite ore can be recrystallized by caustic digestion into an aluminum-rich version of the chabazite structure with Si/Al that can approach 1.0 [26]. The more siliceous phases of the chabazite ore, clinoptilolite and erionite, selectively dissolve in the alkaline medium, reforming with the chabazite as an apparent template. Such semi-synthetic high aluminum chabazite analogs manifest an increase in cation exchange capacity, such as greater than about 5 meq/g and as high as about 7.0 meq/g, and demonstrate high selectivity towards heavy metals from solution, especially lead [27].

Therefore, in one embodiment, sodium Bowie chabazite ore may be reformed and upgraded in an alkaline medium to a semi-synthetic purified, upgraded chabazite with elemental compositions resembling the original chabazite component of the ore (Si/Al~3.0-3.5), if substantial excess soluble silica is present in the reaction/digestion medium. In this process, essentially all of the clinoptilolite and much of the erionite is dissolved and reformed into chabazite, but not at the high aluminum content found in solely caustic digestion. This novel, semi-synthetic, purified and upgraded chabazite is stable towards the rigorous dehydration needed to activate it as an adsorbent. Also, if the process is conducted on granules of the chabazite ore (which are of generally poor mechanical strength) the granules gain greatly in mechanical strength as the clinoptilolite and erionite, which are recrystallized into chabazite, appear to bind the edges of the existing chabazite platelets.

These more uniform, upgraded semi-synthetic chabazites show an enhanced propensity to form uniform dispersions of metal nanodots (such as silver) on their surfaces compared to the raw chabazite ore from which they are derived. In addition, they appear to have enhanced adsorbent properties for molecules such as water and form stronger acid sites (in the H form).

The novel metallic nanodots supported on chabazite may have many possible uses which exploit the macro and nano properties of the metallic element. In one embodiment of a silver nanoparticulate material, they may be used to capture elemental mercury from a process stream, such as from coal-fired power plant flue gas. In another embodiment of a silver nanoparticulate material, they may be used as a novel anti-microbial agent.

EXAMPLES

Example 1

Chabazite

Sedimentary chabazite from the well-known deposit at Bowie, Ariz. was utilized as the zeolite support, obtained from GSA Resources of Tucson, Ariz. [21]. Aluminum enriched chabazites were prepared by prolonged digestion of the raw ore in alkaline silicate mixtures for 1-3 days at 80° C. The degree of aluminum enrichment was governed by the amount of excess alkalinity available during the digestion and recrystallization process.

Figure 1B:
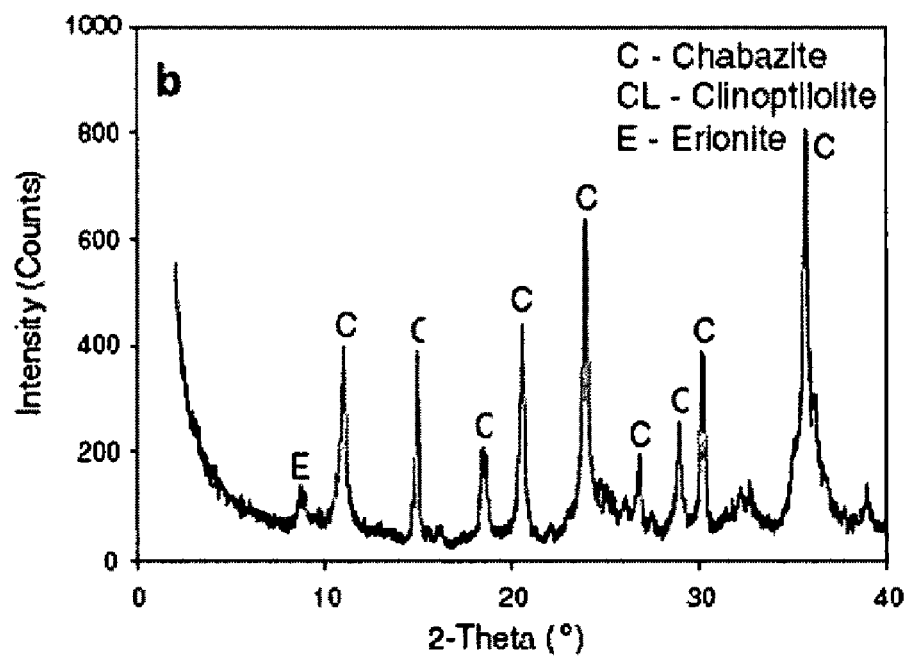

Phase identification of chabazite and aluminum enriched analogs was conducted by X-ray diffraction analysis using a Rigaku Geigerflex Model 2173 diffractometer unit. As is typical of samples from the Bowie deposit, XRD analysis indicated that the material was highly zeolitized with chabazite being the dominant phase. The material also contained significant clinoptilolite and erionite as contaminants as seen in FIG. 1A. Caustic digested enhanced or aluminum enriched materials were found to gain intensity for the chabazite-like peaks while losing all clinoptilolite and a substantial portion of the erionite during the upgrading process, as can be seen by comparing FIGS. 1A and 1B.

Example 2

Formation of Silver Nanodots

Silver ion-exchange was accomplished by exposure of the zeolites as 200 mesh powders to an excess of aqueous silver nitrate at room temperature with stirring for 1 hour. The exchanged materials were thoroughly washed with deionized water, and dried at 100° C. To convert the silver ions in the zeolite to supported metallic silver nanoparticles, the ion-exchanged chabazite was annealed at temperatures ranging from 150° C. to 450° C., for periods of 1-4 h in air.

Quantitative elemental analyses of the silver exchanged materials were conducted using Perkin Elmer Elan6000 quadrupole ICP-MS. Semi-quantitative elemental analysis of the material surfaces was conducted by XPS utilizing a Kratos AXIS 165 spectrometer using monochromated Al Kα (hv=1486.6 eV) radiation in fixed analyser transmission (FAT) mode. The pressure in the sample analysis chamber was less than $10^{-7}$ Pa ($10^{-9}$ torr). Powder samples were mounted on stainless steel sample holders using double-sided adhesive tape. Pass energies of 160 eV and 20 eV were used for acquiring survey and high resolution narrow scan spectra, respectively. An electron flood gun was used to compensate for static charging of the sample. The binding energies of the spectra presented here are referenced to the position of the C is peak at 284.5 eV. Data acquisition and peak fitting were performed by CASA-XPS software.

Figure 2:
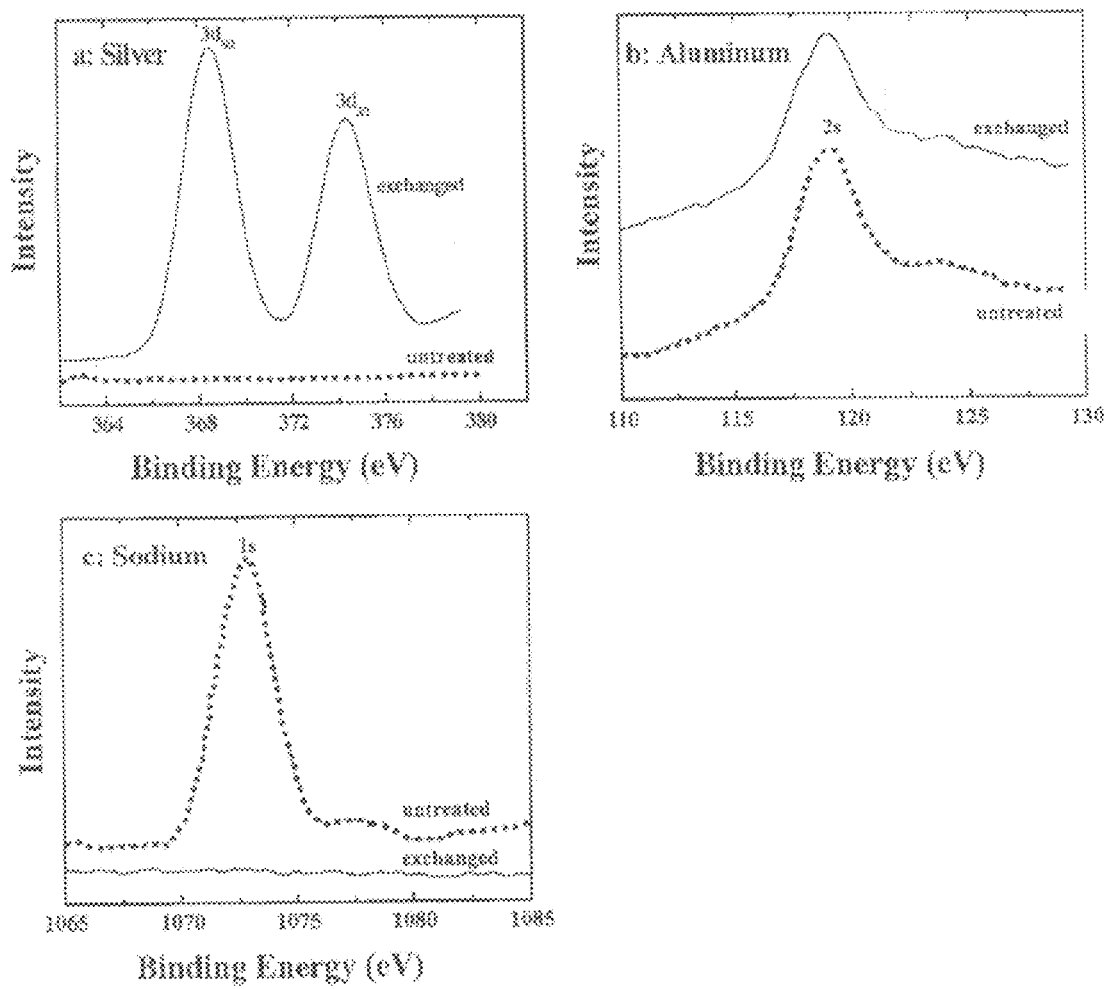
FIG. 2 shows XPS spectra of silver, aluminum, and sodium respectively, in untreated and silver ion-exchanged chabazite.

Successful ion exchange was confirmed by XPS. FIG. 2 shows the intensity (given in arbitrary units) versus binding energy XPS spectra for the untreated (dotted line) and the ion-exchanged (solid-line) chabazite. An intensity shift between the two spectra was added to separate the peaks which would otherwise overlap. As shown by the spectra in FIG. 2, silver is present on the surface of the silver-exchanged chabazite but is absent on the surface of the untreated chabazite.

The nanoparticle composition was confirmed as essentially pure silver using ultra-fine probe energy dispersive X-ray spectroscopy (EDXS) analysis. The binding energy of the 3d5/2 photon electrons in the XPS spectrum confirms that silver is predominantly in the metallic state. Besides silver, the particles also contain trace amounts of aluminum and iron, although we were unable to quantify them. Due to the technique employed, it is also possible that other contaminants such as Na, C, Al and Si may be present in small amounts.

To examine the extent of silver ion exchange with sodium, the narrow spectra of aluminum and sodium were also acquired, as shown in FIG. 2. Both the original and the ion-exchanged chabazite exhibited a similar aluminum spectrum in both band positions and peak intensity. It is evident that within the detection limit of XPS, the ion exchange of sodium by silver on the chabazite is complete. This is indicated by the absence of a sodium band on the spectrum of silver exchanged material.

Both XPS and ICP-MS indicated a silver loading on the order of 20-21 wt. %. Also, there was essentially a complete lack of sodium which would be expected with quantitative exchange. The chabazite platelets are so thin that bulk and surface analyses may be viewing the same portion of the sample and equivalent analyses might be expected. A silver content of slightly in excess of 20 wt. % of the total sample is consistent with the ~2.5 mequiv/g exchange capacity expected for this material.

Example 3

Electron Microscopy

Transmission electron microscopy (TEM) was performed on a Philips Tecnai F20 Twin FEG, equipped with EDX, EFTEM/EELS, Annular Dark field Detector (ADF), and high angle tilting capability, located at the University of Calgary. The microscope was operated in scanning transmission (STEM) mode. Samples were prepared by dry grinding and dispersing materials onto copper grids. Quantitative particle size analysis was performed using SPIP™ microscopy image processing software.

Figure 3:
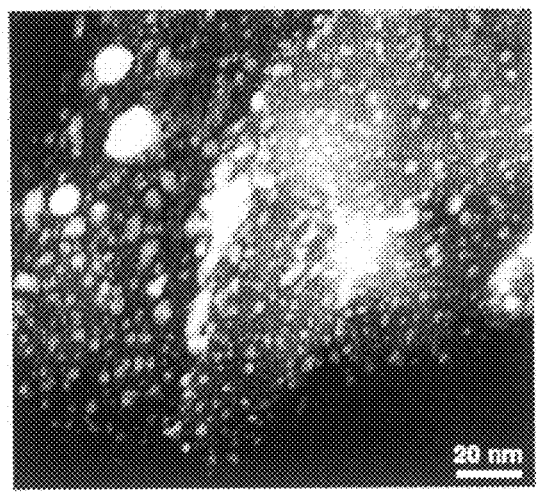
FIG. 3 shows annular dark-field STEM micrographs of silver nanodots residing on the surface of the chabazite support (low-magnification image showing overall Ag dispersion)
Figure 4:
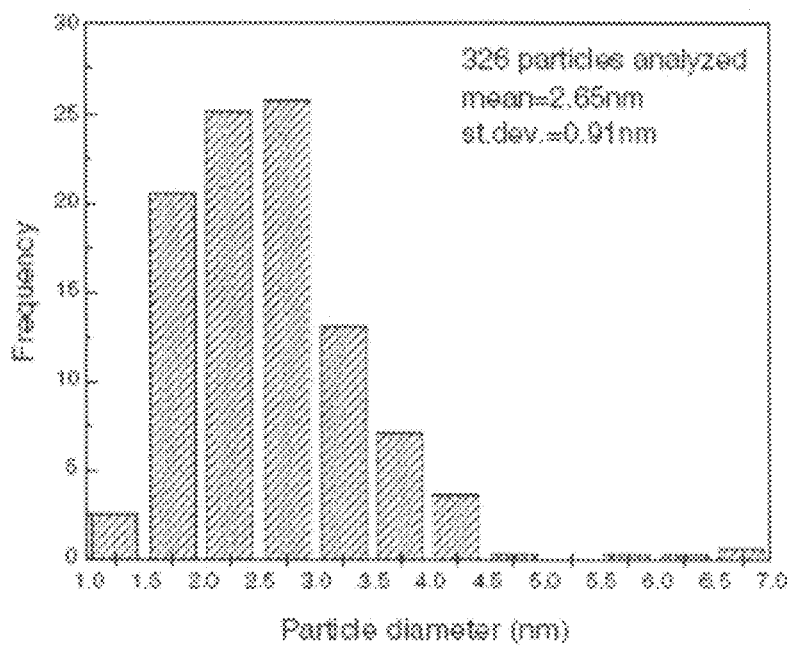
FIG. 4 shows a particle diameter distribution of the silver nanodots shown in FIG. 3.
Figure 5:
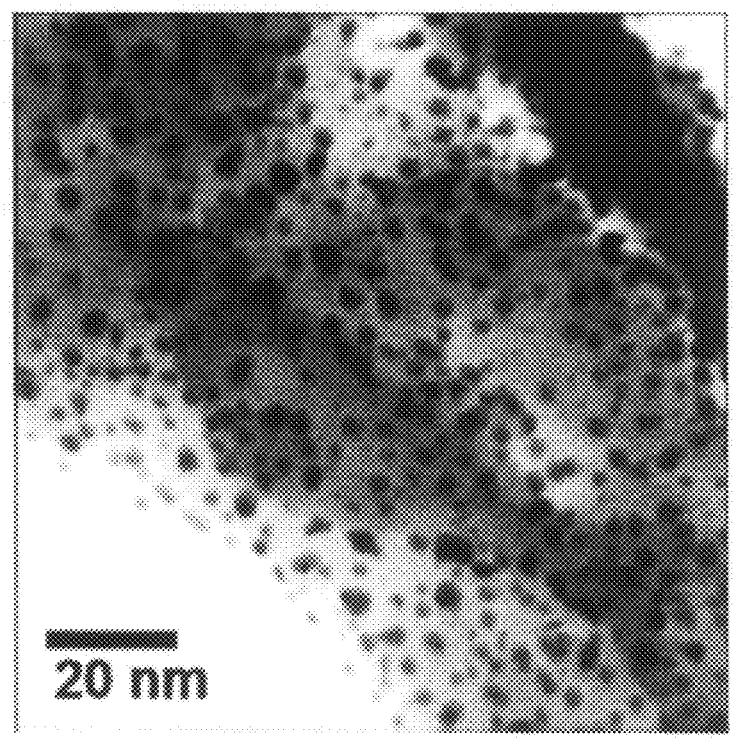
FIG. 5 shows a higher magnification image illustrating the size of the individual nanodots shown in FIG. 3.

Transmission electron microscopy (TEM) analysis, as seen in FIG. 3, illustrates the silver nanoparticle distribution on the mineral chabazite sample. Quantitative particle size analysis, shown in FIG. 4, reveals that the vast majority of the silver nanoparticles are in the order of about 1 to about 5 nm in diameter, with a mean of 2.6 nm. As seen in FIG. 5, higher magnification appears to show the silver as spherical nanodots resting on the chabazite surfaces, although other globular morphologies can not be excluded. The distribution of silver is generally homogeneous, although there are occasional regions in the microstructure that have an irregular particle size and spacing, including some apparent larger pools of metal. This may be due to irregularities in the composition of the mineral substrate.

Example 4

Auger Microscopy

Auger microscopy was performed by a JEOL JAMP-9500F Field Emission Scanning Auger Microprobe. The instrument was equipped with a field-emission electron gun and hemispherical energy analyzer. Identically prepared powders were used for the microprobe analysis as for the TEM.

Figure 6:
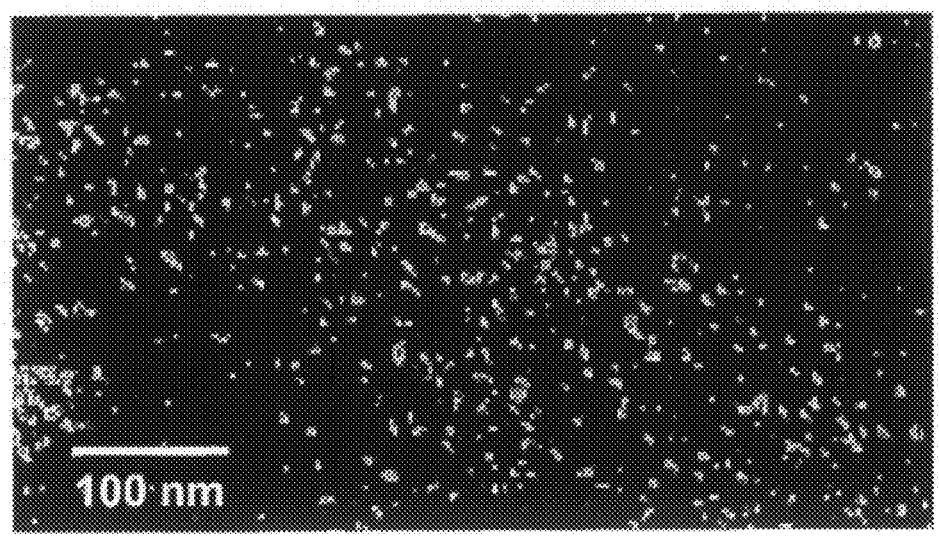
FIG. 6 shows a scanning Auger microscope mapping silver distribution on the chabazite surface.

Auger microscopy mapping confirmed the lateral distribution of silver nanodots. While separately imaging the individual clusters was below the resolution limit of the microscope (the theoretical and practical resolution limits were 10 nm and 20 nm, respectively), we were able to demonstrate a uniform silver distribution on the chabazite surface. FIG. 6 shows a scanning Auger microprobe image of the Ag distribution on the chabazite surface. The silver particles appear slightly larger in the microprobe images relative to the TEM-obtained results. Their distribution also appears less dense. The number density difference may be attributed to the fact that a TEM image shows a minimum of two surfaces (chabazite is a finely layered structure where there are likely more than two surfaces present in each electron transparent sample), while an Auger image simply shows the top surface. The larger apparent particle size may be partly due to the inferior spatial and analytical resolution of the microprobe relative to the TEM, since out-of-focus particles appear larger, while sufficiently fine clusters go undetected.

The Auger results do indicate that a significant fraction of the silver is definitely on the surface in the form of nanodots.

Example 5

Use to Capture Mercury

Chabazite supported silver nanoparticles as formed above were tested on the ability to capture $Hg^0$ (elemental mercury) at elevated temperatures. The capture of elemental mercury from many coal-fired power plant flue gas streams is extremely difficult via established methods. Existing methods are best suited to capture oxidized mercury species formed as flue gases cool from furnace temperatures [22]. Drawbacks of existing adsorbents include an undefined and irreversible capture mechanism, solid waste stream disposal concerns, and the limitations imposed by the elevated temperatures of industrial process gases. These concerns would be eliminated with adsorbent materials that could intercept elemental mercury at realistic process gas temperatures (up to 150° C.).

Elemental mercury ($Hg^0$) breakthrough studies were conducted by passing UHP Argon carrier gas at 40 ml/min through a 3 mm I.D. borosilicate glass chromatographic column. The column contained a 2 cm bed of the test sorbent, held in place with muffled quartz glass wool, and maintained at test temperature for the duration of the experiment. $Hg^0$ vapour standards (50 μL) were injected by a syringe upstream of the sorbent column, and were quantified using standard temperature data. Any mercury breakthrough from the sorbent continued downstream to an amalgamation trap. The trap was thermally desorbed at appropriate intervals. Elemental mercury was detected by Cold Vapour Atomic Fluorescence Spectroscopy (Tekran). Data processing was conducted with Star Chromatography Workstation Ver. 5.5 (Varian, Inc.).

Figure 7:
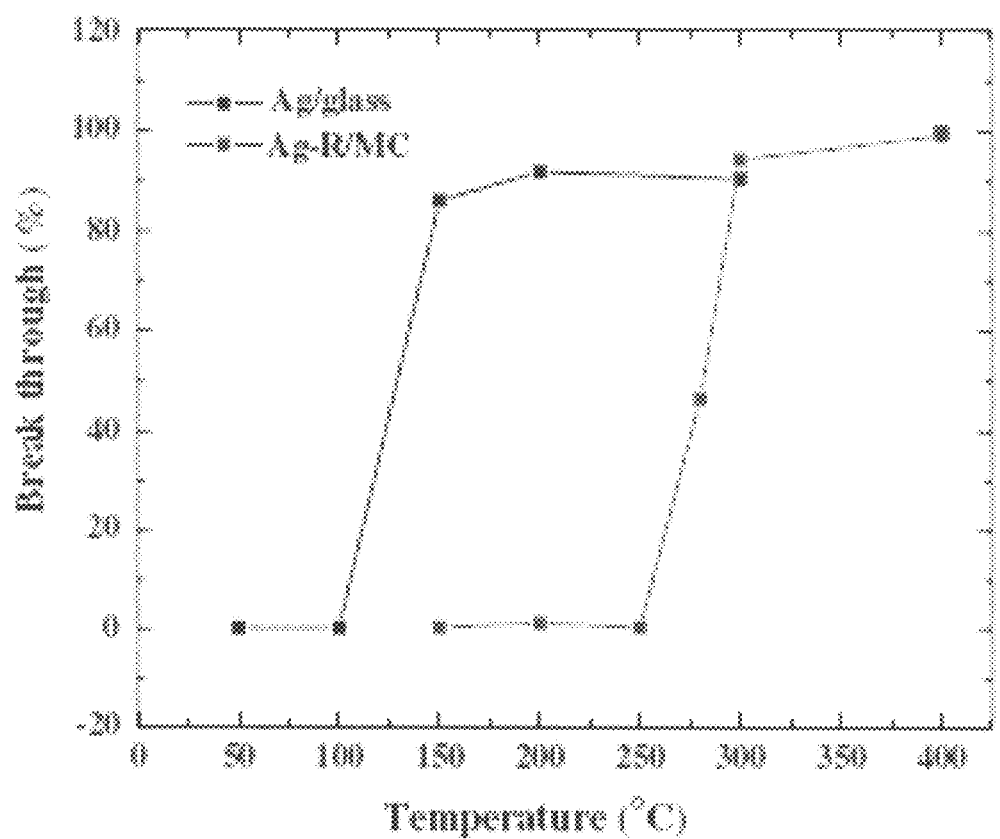
FIG. 7 shows elemental mercury breakthrough on silver nanodots covered chabazite, compared with mercury breakthrough using silver coated glass beads.

We injected mercury as pulse exposures at much higher concentration (4 orders of magnitude) than those found in typical coal-fired power plant flue gases which range from 1-10 $g/m^3$ [23]. FIG. 7 compares elemental mercury breakthrough at various capture temperatures for silver nanoparticles covered chabazite against bulk metallic silver deposited on glass beads. For the case of nanoparticles covered chabazite, breakthrough of elemental mercury is negligible up to capture temperatures of 250° C. Between 250° C. and 300° C., there was partial breakthrough of elemental mercury. Above 300° C., breakthrough becomes complete. At 400° C., release of adsorbed elemental mercury occurred within 5 min. Bulk silver on glass beads was not an effective adsorbent for elemental mercury (FIG. 7). Substantial breakthrough is noted at any temperature above 100° C., limiting its potential utility in flue gas applications. This appears to be a clear demonstration of "nano" enhanced properties derived from an economical, easy to prepare chabazite supported silver nanoparticle materials.

Example 6

Silver Nanodots as an Anti-Microbial Substance

Figure 8:
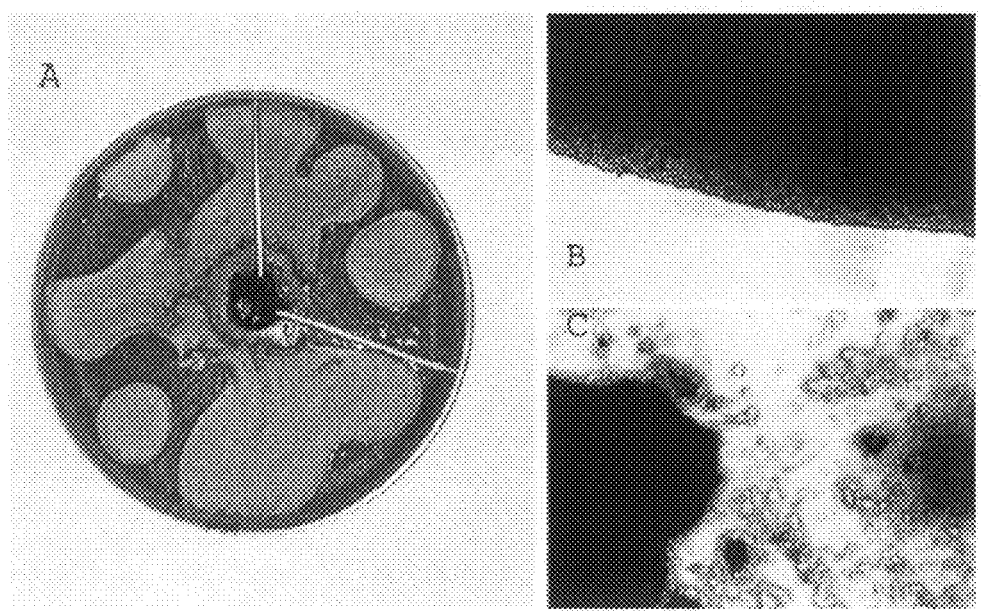
FIG. 8 shows yeast cells on solid malt dextrose agar exhibit a strong zone of inhibition surrounding a centre well containing nanosilver zeolite (a). Cells along the colony edges show normal thick, structured growth (b) in contrast with the fungicidal zone of inhibition (c).

The chabazite platform may also offer a cost effective method to generate medical nanosilver. Yeast grown on agar plates, at concentrations up to 1000 ppm silver nitrate show fungi static control (i.e. retarding fungal growth) but did not create a clear zone of inhibition in the medium. Silver nitrate addition rapidly blackens the medium. By contrast the chabazite supported silver nanodots were observed to be fungicidal, killing and preventing growth. No such antifungal properties were observed for chabazite samples without the silver nanoparticles. In FIG. 8, a clear kill zone is seen surrounding the center well containing the chabazite supported silver nanodots. Unlike silver nitrate containing cultures, the zone of inhibition remained clear, not turning black. This suggests that the active silver species coming from the nanoparticles are different from the ionic silver emanating from silver nitrate. Potentially desirable features of such fixed or supported nanosilver particles include effective localized microbial control based on concentrating highly uniform ensembles of exposed silver particulates in fixed locations. Such localized concentration control is unavailable in many other forms of silver.

Example 7

Upgraded Chabazite

Chabazite ore may be "recrystallized" to form aluminum rich analogs by digestion in alkaline medium. Under certain conditions, maximum aluminum analogs can be prepared [26, 27]. The aluminum content can be boosted substantially by prolonged digestion in a caustic silica mixture. An aluminum enriched chabazite sample was prepared with a Si/Al ratio of about 1.2 and thoroughly silver exchanged as above. Ion exchange of sodium by silver on the enriched chabazite was complete as indicated by the absence of a sodium band on the XPS spectrum of the silver exchanged material. Both XPS and ICP-MS indicated a silver content in the range of 40-42 wt. % of the total sample. This is consistent with the ~6.5 mequiv/g exchange capacity expected for this aluminum enriched chabazite analog.

Figure 9A:
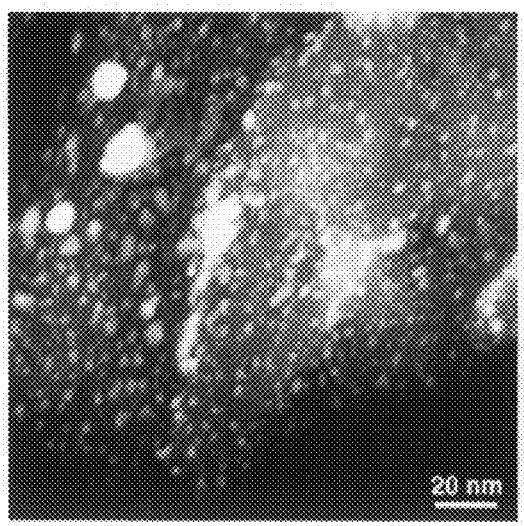
FIG. 9A shows annular dark field STEM micrographs of silver nanodots on raw chabazite.
Figure 9B:
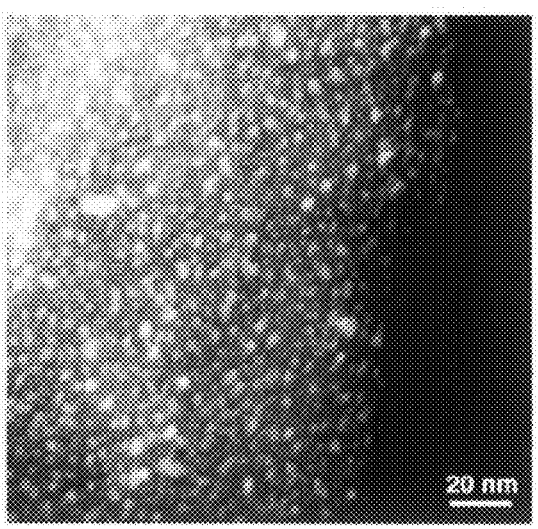
FIG. 9B shows silver nanodots on aluminum enriched chabazite analog.

Thermal reduction of this upgraded, aluminum enriched chabazite analog in air at 300° C. yielded a material with essentially identical silver nanodots as seen on the surface of the mineral chabazite ore. But, the silver nanodots appear to be more uniform and at much higher concentration as seen in FIGS. 9A and 9B. A concentration of 48 nanoparticles per 1000 $nm^2$ was observed for the aluminum enriched material compared to 29 per 1000 $nm^2$ for the silver bearing raw ore. Also, there appears not to be larger pools of metal on the upgraded material as seen in the impure ore.

Figure 10A:
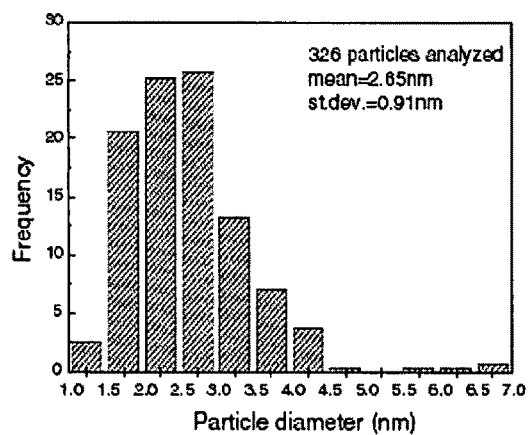
FIG. 10A shows particle diameter distribution of the silver nanodots on mineral chabazite.
Figure 10B:
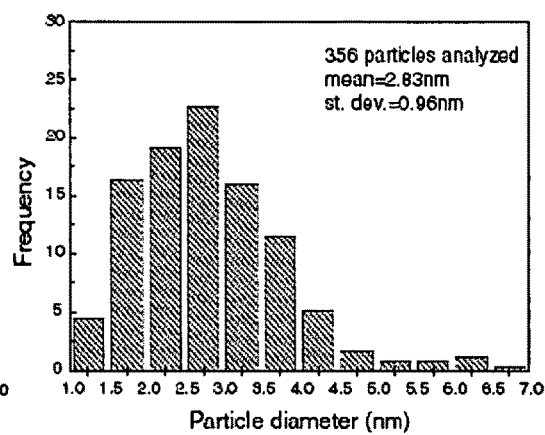
FIG. 10B shows particle diameter distribution of silver nanodots on aluminum enriched chabazite analog.

Quantitative surface analysis indicated silver nanoparticles that were (perhaps) slightly larger on the aluminum enriched material than on the raw chabazite ore. As seen in the particle size distribution shown in FIGS. 10A and 10B, the mean particle size for the latter was 2.65 nm compared to 2.83 nm for the former.

REFERENCES

The following references are referred to in square brackets above, and the contents of these references are incorporated herein as if reproduced in their entirety.

[1] R. Jin, Y. Cao, E. Hao, G. C. Metraux, G. C. Schatz, C. A. Mirkin, Nature 425 (2003) 287.
[2] R. Jin, Y. Cao, C. A. Mirkin, K. L. Kelly, G. C. Schatz, J. G. Zheng, Science 294 (2001) 1901.
[3] A. Callegari, D. Tonti, M. Chergui, Nano Lett. 3 (2003) 1565.
[4] Y. Sun, B. Mayers, Y. Xia, Nano Lett. 3 (2003) 675.
[5] Y. Sun, Y. Xia, Adv. Mater. 15 (2003) 695.
[6] S. Chen, D. L. Carroll, Nano Lett. 2 (2002) 1003.
[7] Y. Zhou, C. Y. Wang, Y. R. Zhu, Z. Y. Chen, Chem. Mater. 11 (1999) 2310.
[8] M. J. Edmondson, W. Zhuo, S. A. Sieber, I. P. Jones, I. Gameson, P. A. Anderson, P. P. Edwards, Adv. Mater. 13 (2001) 1608.
[9] C. R. Li, X. N. Zhang, Z. Zhang, Mater. Lett. 58 (2004) 27.
[10] L. M. Worboys, P. A. Anderson, in: E. van Steen, L. H. Callanan, M. Claeys (Eds.), Recent Advances in the Science and Technology of Zeolites and Related Materials, Parts A, B, C, Studies in Surface Science and Catalysis, vol. 154, 2004, p. 931.
[11] M. Tsapatsis, AIChE J. 48 (2002) 654.
[12] R. Strohal, M. Schelling, M. Takacs, W. Jurecka, U. Gruber, F. Offner, J. Hospital Infect. 60 (2005) 226.

[13] R. E. Burrell, L. R. Morris, P. S. Apte, S. B. Sant, K. S. Gill, U.S. Pat. No. 5,837,275 (1998).
[14] G. S. Metraux, C. A. Mirkin, Adv. Mater. 17 (2005) 412.
[15] L. R. Gellens, W. J. Mortier, J. B. Uytterhoeven, Zeolites 1 (1981) 85.
[16] V. S. Gurin, V. P. Petranovskii, N. E. Bogdanchikova, Mater. Sci. Eng. C 19 (2002) 327.
[17] V. S. Gurin, V. P. Petranovskii, N. E. Bogdanchikova, Mater. Sci. Eng. C 23 (2003) 81.
[18] V. S. Gurin, V. P. Petranovskii, M.-A. Hernandez, N. E. Bogdanchikova, A. A. Alexeenko, Mater. Sci. Eng. A 391 (2005) 71.
[19] G. Bagnasco, P. Ciamgelli, E. Czaran, J. Rapp, G. Russo, in: P. A. Jacobs, D. Forschungsgemeinschaft (Eds.), Metal Microstructures in Zeolites, Elsevier, Amsterdam, 1982.
[20] S. J. Cho, J. E. Yie, R. Ryoo, Catal. Lett. 71 (2001) 163.
[21] GSA Resources Inc. http://gsaresources.com.
[22] B. Hall, O. Lindqvist, E. Ljungstrom, Environ. Sci. Technol. 24 (1990) 108.
[23] S. J. Miller, G. E. Dunham, E. S. Olson, T. D. Brown, Fuel Proc. Tech. 65-66 (2000) 343.
[24] V. Alt, T. Bechert, P. Steinrucke, M. Wagener, P. Seidel, E. Dingeldein, E. Domann, R. Schnettler, Biomaterials 25 (2004) 4383.
[25] K. A. Thrush, S. M. Kuznicki, J. Chem. Soc. Faraday Trans. 87 (1991) 1031.
[26] S. M. Kuznicki, J. R. Whyte, Jr., U.S. Pat. No. 5,071,804 (1991).
[27] S. M. Kuznicki, J. R. Whyte, Jr., U.S. Pat. No. 5,223,022 (1993).
[28] P. J. Maroulis, C. G. Coe, S. M. Kuznicki, D. A. Roberts, U.S. Pat. No. 4,747,854 (1988).
[29] P. J. Maroulis, C. G. Coe, S. M. Kuznicki, P. J. Clark, D. A. Roberts, U.S. Pat. No. 4,744,805 (1988).
[30] D. T. Hayhurst, in L. B. Sand, F. A. Mumpton (Eds.), *Natural Zeolites: Occurrence, Properties, Use Permagon Press*, 1978, 503.
[31] Ch. Baerlocher, W. M. Meier, D. H. Olson, *Atlas of Zeolite Framework Types, fifth rev. ed.*, Elsevier, Amsterdam, 2001.
[32] D. W. Breck, *Zeolite Molecular Sieves*, John Wiley, New York, 1974.

What is claimed:

1. A method of forming metal nanodots having a size less than about 100 nm, comprising the steps of: (a) performing ion-exchange with a solution of the metal ions and an upgraded chabazite material substantially free of clinoptilolite and erionite; and (b) converting the metal ions in the chabazite to metal nanodots by annealing the chabazite in air at a temperature greater than about 100° and less than about 500° C.

2. The method of claim 1 wherein the metal comprises silver, copper, nickel, gold or a member of the platinum group.

3. The method of claim 2 wherein the metal comprises silver.

4. The method of claim 1 wherein the conversion step is performed at a temperature greater than about 100° and less than about 400° C.

5. The method of claim 1 wherein the chabazite material comprises chabazite powder.

6. The method of claim 1 wherein the upgraded chabazite has a Si/Al ratio of about 3.0 to about 3.5.

7. The method of claim 1 wherein the upgraded chabazite is produced by alkaline digestion of naturally occurring chabazite.

8. The method of claim 1 wherein the upgraded chabazite comprises synthetic chabazite.

9. The method of claim 3 wherein the silver nanodots have a mean particle size of less than about 5 nm.

* * * * *